(12) United States Patent
Van Eupen et al.

(10) Patent No.: US 10,253,031 B2
(45) Date of Patent: Apr. 9, 2019

(54) STABLE PEMETREXED ARGININE SALT AND COMPOSITIONS COMPRISING IT

(71) Applicant: SYNTHON B.V., Nijmegen (NL)

(72) Inventors: Jacobus Theodorus Henricus Van Eupen, Nijmegen (NL); Borek Zaludek, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 15/989,751

(22) Filed: May 25, 2018

(65) Prior Publication Data

US 2018/0298014 A1    Oct. 18, 2018

Related U.S. Application Data

(63) Continuation of application No. 14/898,433, filed as application No. PCT/EP2013/062413 on Jun. 14, 2013.

(51) Int. Cl.
C07D 487/04 (2006.01)
C07C 277/00 (2006.01)
C07C 279/14 (2006.01)

(52) U.S. Cl.
CPC .......... *C07D 487/04* (2013.01); *C07C 277/00* (2013.01); *C07C 279/14* (2013.01)

(58) Field of Classification Search
CPC .................................................. C07D 487/04
See application file for complete search history.

(56) References Cited

U.S. PATENT DOCUMENTS

| | | |
|---|---|---|
| 5,344,932 A | 9/1994 | Taylor |
| 5,416,211 A | 5/1995 | Barnett et al. |
| 6,262,262 B1 | 7/2001 | Kjell |
| 7,138,521 B2 | 11/2006 | Chelius et al. |
| 8,088,919 B2 | 1/2012 | Busolli et al. |

FOREIGN PATENT DOCUMENTS

| | | |
|---|---|---|
| EP | 432677 | 6/1991 |
| EP | 23517655 | 8/2011 |
| WO | WO 2008/021410 A2 | 2/2008 |
| WO | WO 2008/124485 | 10/2008 |

OTHER PUBLICATIONS

Yu et al., Chem Abstracts "Antitumor parenteral liquids containing pemetrexed and antioxidant", STN Database accession # 2007:1401791 (2007).*
Mao et al., CHem Abstracts "Preparation of pemetrexed ethylenediamine salt", STN Database accession # 2007:1022904 (2007).*
U.S. Appl. No. 14/898,433, filed Dec. 14, 2015.*
Abstract for CN Patent Appl. No. 2006-10044324, EPO Database Patent Search, XP-002701508, Nov. 7, 2013
Abstract for CN Patent Appl. No. 2006-10024564, EPO Database Patent Search, XP-002701509, Nov. 7, 2013.

* cited by examiner

*Primary Examiner* — Paul V Ward
(74) *Attorney, Agent, or Firm* — Buscher Patent PLLC

(57) ABSTRACT

The present invention relates to arginine salt of pemetrexed of formula (1), (1)

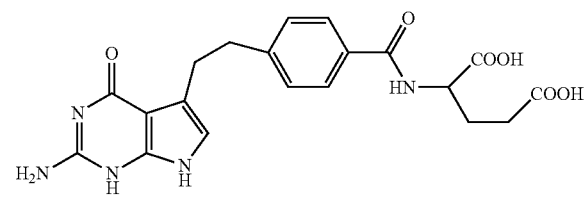

particularly to a stable solid form thereof, and to pharmaceutical compositions comprising such salt.

17 Claims, No Drawings

STABLE PEMETREXED ARGININE SALT AND COMPOSITIONS COMPRISING IT

CROSS REFERENCE TO RELATED APPLICATIONS

The present application is a continuation under 35 U.S.C. § 120 of copending U.S. application Ser. No. 14/898,433, filed Dec. 14, 2015, which is a U.S. national stage application under 35 U.S.C. § 371 of PCT International Application No. PCT/EP2013/062413, which was filed on Jun. 14, 2013, the disclosure of which is incorporated by reference herein in its entirety.

Pemetrexed is a common name for compound N-[4-[2-(2-amino-4,7-dihydro-4-oxo-1H-pyrrolo [2,3-d]pyrimidin-5-yl)ethyl]benzoyl]-L-glutamic acid of formula (1)

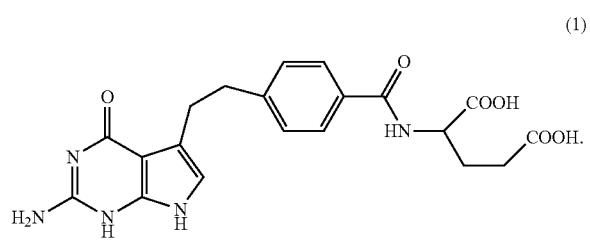 [SMILES: Nc1nc(=O)c2c(CCc3ccc(C(=O)NC(CCC(=O)O)C(=O)O)cc3)c[nH]c2[nH]1]

(1)

The compound has been first disclosed in EP 432677.

Pemetrexed is a pharmaceutically active compound, which is used, i.e., in the treatment of malignant pleural mesothelioma and non-small cell lung cancer.

As pemetrexed of the above formula (1) is a bivalent acid (a diacid) comprising two carboxylic groups. It may form various types of salts with bases. On the other hand, pemetrexed has basic nitrogens and, accordingly, it may form acid addition salts with various acids. The commercially available product, sold, e.g., under the brand name ALIMTA by Eli Lilly, comprises hydrated disodium salt of pemetrexed as the active substance and is supplied as a sterile lyophilized powder for intravenous infusion available in single-dose vials. The preparation of lyophilized pemetrexed disodium composition is disclosed in U.S. Pat. No. 7,138,521.

U.S. Pat. No. 7,138,521 also describes a stable crystalline heptahydrate form of pemetrexed disodium having a characteristic X-ray diffraction pattern. The patent states that pemetrexed disodium can exist in the form of a heptahydrate which is much more stable than the previously known 2.5 hydrate and shows that the primary advantage of the heptahydrate crystalline form over the 2.5 hydrate crystal form is its stability and also with respect to formation of related substances. It also shows that when the heptahydrate is subjected to elevated temperatures, low humidity, and/or vacuum, it converts to the 2.5 hydrate crystal form by loss of water.

The above patent shows that problems may arise because of conversions between different crystalline forms (actually the above mentioned forms are different hydrates, not polymorphic forms) of pemetrexed when exposed to elevated temperatures, low humidity, etc. Formulation processes may involve a variety of the above mentioned adverse conditions, resulting in a possibility that the stability of the final product may be affected.

Disodium salt of pemetrexed is soluble in water, contrary to the pemetrexed diacid of the above formula (1). Formulating water soluble pemetrexed salts, however, has not proven to be an easy task, due to its stability issues. The infusion solution has to be prepared immediately before use, by dissolving the content of the single-dose vial in water and diluting the obtained solution with an infusion liquid. The relatively rapid formation of degradants is the main factor which has, so far, prevented ready-to-use aqueous pemetrexed formulations from being commercially available. According to WO 2012/015810, five major degradants of pemetrexed have been observed. Under acidic conditions, decarboxylation of glutamic acid is observed. Under alkaline conditions, degradation proceeds by side chain amide hydrolysis followed by deamination. In the presence of oxygen, two oxidative degradants result.

There remains a need for preparing alternate pemetrexed formulations with sufficient stability. In particular, it would be advantageous to find alternate pemetrexed salts, which may preferentially exist in an amorphous form to prevent polymorphic transitions, which may occur during storage and formulation of crystalline forms. It is known that amorphous forms of active ingredients can be relatively more unstable, when compared with crystalline forms. Thus, finding an alternate amorphous form of pemetrexed with sufficient inherent stability is desirable as it would break a prejudice against using pemetrexed in amorphous form.

BRIEF DESCRIPTION OF THE INVENTION

The present invention relates to a novel pemetrexed salt, which may advantageously exist in an amorphous form and is sufficiently stable for formulation in pharmaceutical formulations, particularly lyophilized formulations.

In the first aspect, the invention relates to arginine salt of pemetrexed, in particular to a salt of the formula (2)

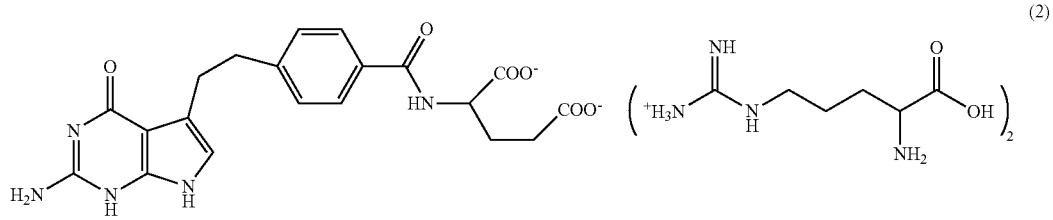

(2)

In a particular aspect, the arginine salt is in solid form, advantageously in an amorphous form.

In the second aspect, the invention relates to a pharmaceutical composition comprising arginine salt of pemetrexed and at least one pharmaceutically acceptable excipient. Preferably, the pharmaceutical composition is a solid composition. Yet preferably, the composition comprises the arginine salt of pemetrexed in an amorphous form. In a particular aspect, the pharmaceutical composition is a lyophilized powder useful for reconstitution into an infusion solution by an infusion liquid.

In a third aspect, the invention relates to a process for making arginine salt of pemetrexed comprising combining pemetrexed diacid of formula (1) with L-arginine in a solution and removing the solvent. In a particular aspect, the removal of the solvent is carried out by evaporation or lyophilization.

In a fourth aspect, the invention relates to a process for making a pharmaceutical composition, advantageously a solid pharmaceutical composition, comprising a step of combining arginine salt of pemetrexed with at least one pharmaceutically acceptable excipient. In a particular aspect, the combining step comprises providing the arginine salt of pemetrexed, contacting it with excipient(s) in a solvent and removing the solvent. In yet another particular aspect, the step of providing the arginine salt of pemetrexed comprises mixing pemetrexed diacid with arginine in a solvent.

DETAILED DESCRIPTION OF THE INVENTION

The present invention relates to arginine salt of pemetrexed, particularly to a stable solid form thereof, and to pharmaceutical compositions comprising such salt.

The in-house study of possibilities of making various salts of pemetrexed has revealed that it is difficult to prepare solid state forms of salts of pemetrexed with various amines. Instead, oily products are often formed. It was, however, found with surprise that pemetrexed of formula (1) may be combined with basic amino-acids, particularly with L-arginine of formula (3)

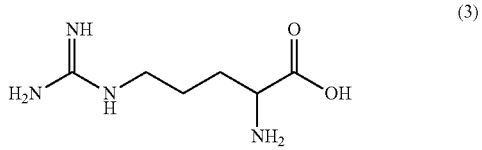 [SMILES: N=C(N)NCCCC(N)C(=O)O]

(3)

(Hereinafter only: arginine) to form a stable solid compound. Advantageously, the molar ratio between pemetrexed and arginine moieties in the compound is 1:1 or 1:2. A compound having 1:2 molar ratio between both moieties is the preferred compound and it is believed that the product comprising the moieties in the above ratio is bis-arginine salt of pemetrexed of the formula (2) above.

Regardless of the actual structure, the compound of the present invention defined above and preparable by the process shown below is denominated throughout the invention as "arginine salt of pemetrexed".

The solid compound of the above formula (2) may exist in a crystalline form or in an amorphous form, whereby the amorphous form is considered advantageous for pharmaceutical applications. The compound is soluble in water at ambient conditions, wherein the solutions thereof are pH neutral and thus suitable for pharmaceutical applications. The compound is also sufficiently stable in solid, particularly amorphous, state, both in its isolated form and, as well in solid pharmaceutical compositions. The term "stable" relates to both chemical and physical stability.

Arginine salt of pemetrexed of the present invention may be prepared by combining pemetrexed diacid with L-arginine in a pre-defined ratio. L-arginine is a naturally occurring aminoacid, which is commercially available.

Pemetrexed diacid of the above formula (1) and its preparation is believed to have been described for the first time in U.S. Pat. No. 5,344,932.

Formation and isolation of pemetrexed diacid from a mixture of water and ethanol having a pH of 2.5-3.5 is disclosed in U.S. Pat. No. 7,138,521. Formation and isolation of pemetrexed diacid from an aqueous solution having a pH of 5 is disclosed in U.S. Pat. No. 5,416,211. Formation and isolation of pemetrexed diacid from an aqueous solution having a pH of 2.8-3.1 is disclosed in U.S. Pat. No. 6,262,262.

Various crystalline forms of pemetrexed diacid as well as methods for obtaining them have been disclosed in U.S. Pat. No. 8,088,919, EP 2351755 and EP 2129674.

Highly pure pemetrexed diacid may be obtained according to a process disclosed in WO2008/021410A2.

The formation of arginine salt of pemetrexed according to various embodiments of the present invention is carried out by combining pemetrexed diacid with arginine in a solution and removing the solvent. The solvent is typically water or a mixture of water with a water soluble organic cosolvent. Advantageously, the water soluble organic cosolvent has boiling point lower than 100° C. In an example, the suitable organic cosolvent may be aliphatic alcohol such as methanol, ethanol or isopropanol, aliphatic ketone such as acetone, cyclic ether such as dioxan or tetrahydrofuran, aliphatic nitrile such as acetonitrile etc., and mixtures thereof. The organic cosolvent, if present, is typically added after a solution of arginine salt of pemetrexed in water is obtained.

Typically, pemetrexed diacid and arginine are combined in 1:1 or 1:2 molar ratio or close to this ratio (such as from 1:0.9 to 1:1.1 or from 1:1.8 to 1:2.2), wherein the 1:2 molar ratio (in ranges from 1:1.8 to 1:2.2 mol/mol) is the preferred one for purpose of pharmaceutical applications.

Advantageously, arginine is first dissolved in water and after that pemetrexed diacid is added to the resulted solution. This results in quicker dissolution of inherently sparingly soluble pemetrexed diacid. Cosolvent, if any, is added afterwards.

The solvent is removed from the mixture by evaporation, advantageously at diminished pressure, by spray-drying or by lyophilization. For purposes of the latter arrangement, the solvent is advantageously water, without presence of an organic cosolvent.

Typically, solid arginine salt of pemetrexed is obtained by the above process substantially in an amorphous form. Such form is characterized in that its XRPD pattern does not exhibit any characteristic diffraction peak. The term "substantially" means at least about 90% of the amorphous form, which includes at least about 95% or in some embodiments at least about 99% of amorphous form.

The solid product may comprise residual water and/or organic solvent. Typically, the product comprises less than 10% of these volatile components.

The solid, particularly amorphous, arginine salt of pemetrexed may be combined in various pharmaceutical compositions. Thus, the present invention also comprises a pharmaceutical composition comprising an arginine salt of pemetrexed, advantageously the salt of formula (2), and at least one pharmaceutically acceptable excipient. Preferably, the pharmaceutical composition is a solid composition. Yet preferably, the arginine salt of pemetrexed is formulated in the composition in an amorphous form. The composition may be advantageously formulated into dosage forms for parenteral applications. In a particular aspect, the pharmaceutical composition is formulated as a lyophilized powder useful for reconstitution into an infusion solution by an infusion liquid.

The pharmaceutically acceptable excipients for purpose of the present invention, particularly those useful for making the lyophilized pharmaceutical formulations, may include one or more of: diluents or bulking agents including one or more sugars such as dextrose, sucrose, mannose, lactose, trehalose and the like, one or more sugar alcohols such as mannitol, xylitol and the like; antibacterial preservatives, including one or more of thiomersal, benzalkonium chloride, benzethonium chloride, chlorobutanol; pH-adjustors such as hydrochloric acid; antioxidants including ascorbic acid, glutathione. L-cysteine, lipoic acid and the like; buffers including one or more of acetate, citrate, tartrate, phosphate, benzoate, and bicarbonate buffers; chelating agents such as disodium edetate; tonicity contributors including one or more of sodium chloride, potassium chloride, dextrose, mannitol, and lactose. The addition of a sugar or sugar alcohol can improve the stability of pemetrexed formulations. Thus, a suitable lyophilized pharmaceutical formulation may comprise pemetrexed arginine salt and at least one sugar or sugar alcohol, advantageously mannitol.

In various advantageous embodiments, the sugar or sugar alcohol is present in amounts from 0.1 g to 2 g per 1 g of pemetrexed arginine salt.

The unit dose of the pharmaceutical formulation typically comprises from 50 to 1500 mg of pemetrexed, calculated as the diacid form. Advantageously, the unit dose comprises 100 mg, 250 mg, 500 mg or 1000 mg of pemetrexed. Thus, in a specific aspect, the invention includes a vial or similar container comprising a dose amount of the composition of the invention. Any suitable sterile vial or container fit for the sterile storage of a pharmaceutical such as pemetrexed for extended periods of time may be used. Suitable containers can be glass vials, polypropylene or polyethylene vials or other special purpose containers.

A further aspect of the invention includes a kit and/or pharmaceutical container for holding the pemetrexed-containing compositions described herein. The kit contains at least one pharmaceutically acceptable vial or container containing one or more doses of the pemetrexed-containing formulations/compositions as well as other pharmaceutically necessary materials for storing and/or administering the drug, including instructions for storage and use, infusion bag or container with an infusion diluent etc.

The solid pharmaceutical composition comprising arginine salt of pemetrexed of the present invention can be made by a process comprising a step of combining an arginine salt of pemetrexed with at least one pharmaceutically acceptable excipient. In a particular aspect, the combining step comprises providing the arginine salt of pemetrexed, e.g. by a process disclosed above, contacting it with the excipient(s) in a solvent and removing the solvent. In yet another particular aspect, the step of providing the arginine salt of pemetrexed comprises mixing pemetrexed diacid with L-arginine in a solvent.

The process of making compositions of the present invention typically comprises a step of weighing the respective ingredients and dissolving them in water, preferably under stirring. Thus, in one embodiment, arginine salt of pemetrexed and at least one excipient listed above are weighed and dissolved in water. In an alternate embodiment, the arginine salt of pemetrexed is prepared in situ by combining pemetrexed free acid with arginine in the desired molar ratio, which typically is 1:1 or 1:2 molar ratio or close to this ratio, wherein the 1:2 ratio (in ranges from 1:1.8 to 1:2.2 mol/mol) is the preferred one.

Advantageously, water is first deoxygenated by a suitable technique, e.g. by saturating it by an inert gas, by deaerating with ultrasound etc.

The dissolution process is preferably conducted in atmosphere of an inert gas such as nitrogen or argon.

In the last stage, pH of the composition is adjusted to the desired value by an acid or base.

The obtained solution is filtered and sterilized and filled into vials comprising the desired amount of pemetrexed per vial.

The arginine salt of pemetrexed is typically present in the solutions in concentrations between 10 and 60 mg/ml, preferably between 15 and 50 mg/ml, when calculated as anhydrous pemetrexed. In alternative aspects, the amount of pemetrexed may be outside these ranges but the amounts will be sufficient for single or multiple administrations of dosages generally regarded as effective amounts.

Water must be of pharmaceutically acceptable quality. Typically, water in quality "for injections", as defined in acknowledged Pharmacopoeias. Is used. In an advantageous aspect, water is the only liquid component present in the compositions.

In an advantageous embodiment of the invention, the adjusted pH value of the solution is from about 6.5 to about 8.5. The suitable pH adjustor may be any suitable pharmaceutically acceptable acid, base, salt or a combination thereof.

In the next step, the solvent, typically water, is removed from the composition. Typically, water is removed by lyophilization (freeze-drying) under suitable conditions. Freeze drying can be conducted at temperatures from about −10 to about −60° C., under vacuum in the range of about 0.5 to about 100 Pa.

In an advantageous embodiment, the subject of the lyophilization process is the content of vials prepared as shown above. Accordingly, the lyophilization process yields a composition comprising the unit dose of pemetrexed, which typically comprises from 50 to 1500 mg of pemetrexed, calculated as the diacid form.

In the last step of the overall process, the vials are closed by a suitable stopper, labeled and packed into suitable container.

The compositions and formulations of the present invention are particularly suited for parenteral administration. For such administration, the composition is reconstituted prior to its use by an appropriate liquid medium. The medium may include sterile water, a pH buffered solution, sodium chloride solution, a dextrose solution or combination of the same.

The compositions of the present invention may be used in medicine, particularly for treating a pemetrexed sensitive disease in mammals. Thus, in yet another aspect of the invention, there are provided methods of treating a pemetrexed sensitive disease in mammals. Pemetrexed sensitive diseases include, but are not limited to, cancers, such as malignant pleural mesothelioma and non-small cell lung cancer. The use or methods include administering an effective amount of a pemetrexed-containing composition as described herein to a mammal in need thereof.

The following examples illustrate the invention.

EXAMPLES

Example 1

To 500 mg of pemetrexed diacid and 407 mg of arginine, 6 ml of water was added. The mixture was stirred until a clear solution was formed. This took approximately 5 minutes. The solvent was evaporated and the residue was dried over night at 40° C. under vacuum.

XRPD test confirmed amorphous character of the product.

TGA curve exhibits gradual mass loss of 4.738% of water between 25 and 220° C.

NMR confirmed the structure of bis-arginine salt (formula (2))

Example 2

1000 mg of pemetrexed (diacid) and 815 mg of arginine was added to 6 ml of water. The mixture was stirred at ambient temperature until a clear solution was formed.

The solution was divided into 6 fractions and the following cosolvents were added to the respective fractions:

| | |
|---|---|
| .01 | 3 ml of methanol |
| .02 | 3 ml of ethanol |
| .03 | 2 ml of isopropanol |
| .04 | 2 ml of acetonitrile |
| .05 | 2 ml of tetrahydrofuran |
| .06 | 2 ml of acetone |

The solutions were evaporated on a rotary vacuum evaporator. The solid residues were dried at 40° C. under vacuum over night.

Analysis of the material by XRPD has proven an amorphous material.

Example 3

Process for making unit dose lyophilized composition (50 mg pemetrexed per vial):

Under inert atmosphere of nitrogen, 875.0 mg of pemetrexed (diacid) was dissolved in a solution of 731.0 mg arginine (2.1 molar equivalents related to pemetrexed) in 30 ml of Water for injections under stirring. After that, 875 mg of mannitol was added and dissolved. The pH was adjusted to about 7.5 by 1 M hydrochloric acid and the weight of the solution was adjusted to 35 gram amount by Water for injections. The solution was filtered through PVDF filter 0.2 microns, filled in clear 10 R vials per 2 grams and freeze dried according to the program presented in the table.

| Process Phase | Duration (hh:mm) | Temperature (° C.) | Vacuum (mbar) | Safety Pressure (mbar) |
|---|---|---|---|---|
| Loading | 00:00 | +5 | | |
| Fast freezing | 01:00 | −45 | | |
| Freezing | 01:30 | −45 | | |
| Freezing | 00:45 | −15 | | |
| Annealing | 01:00 | −15 | | |
| Freezing | 01:30 | −45 | | |
| Freezing | 02:00 | −45 | | |
| Evacuation 1 | 00:10 | −45 | 0.37 | 0.63 |
| Sublimation | 05:00 | +5 | 0.37 | 0.63 |
| Sublimation | 06:15 | +5 | 0.37 | 0.63 |
| Evacuation 2 | 00:10 | +5 | 0.06 | 0.63 |
| Second drying | 05:35 | +30 | 0.06 | 0.63 |
| Second drying | 03:30 | +30 | 0.06 | 0.63 |

A stability study has been performed in order to compare the composition of the present example with the commercial product ALIMTA 100 mg and 500 mg. Impurities present in the pemetrexed-comprising formulations during stability studies performed were detected by high performance liquid chromatography (HPLC) equipped with UV detector at a suitable wavelength (typically 227 nm) and calculated on a normalized peak area response ("PAR.") basis. As an acceptable limit, demonstrating sufficient stability at the corresponding sampling point, the sum of peaks of all individual degradants in the inventive compositions should not exceed 2% of the total PAR. The peak size of any individual degradant should not exceed 1% of the total PAR. In the tables below, the "UN" denotes an unknown impurity, Impurities A, B, C and D have known structure (Ph. Eur.).

The Originator product Alimta was analyzed in the beginning (ZERO time) and after storage at various conditions.

| Alimta 500 mg, Batch A721520E | | | | | |
|---|---|---|---|---|---|
| Name | RRT | Zero | 2 weeks 50° C. | 3 months 40° C./ 75% RH | 6 months 40° C./ 75% RH |
| UN | 0.33 | nd | nd | nd | 0.01 |
| UN | 0.37 | 0.04 | 0.04 | 0.05 | 0.04 |
| UN | 0.39 | nd | nd | 0.01 | nd |
| UN | 0.46 | 0.15 | 0.14 | 0.13 | 0.14 |
| Impurity A | 0.58 | 0.04 | 0.04 | 0.04 | 0.04 |
| Impurity B and C | 0.66 | 0.11 | 0.11 | 0.08 | 0.09 |
| UN | 0.74 | 0.01 | 0.01 | 0.01 | 0.01 |
| UN | 0.88 | 0.01 | nd | 0.01 | 0.02 |
| UN | 0.91 | 0.01 | 0.01 | 0.01 | 0.01 |
| UN | 1.78 | nd | 0.01 | 0.01 | 0.01 |
| ΣIMP (% IN) | | 0.37 | 0.36 | 0.35 | 0.37 |

| Alimta 100 mg, Batch A693326 | | | | | |
|---|---|---|---|---|---|
| Name | RRT | Zero | 2 weeks 50° C. | 1 month 40° C./ 75% RH | 6 months 40° C./ 75% RH |
| UN | 0.34 | 0.02 | nd | nd | nd |
| UN | 0.41 | 0.01 | 0.01 | 0.01 | nd |
| UN | 0.48 | 0.06 | 0.05 | 0.01 | nd |
| UN | 0.50 | nd | nd | 0.02 | 0.05 |
| Impurity A | 0.64 | 0.03 | 0.03 | 0.03 | 0.03 |
| Impurity B and C | 0.72 | 0.04 | 0.04 | 0.03 | 0.03 |
| UN | 0.81 | 0.02 | 0.02 | 0.02 | 0.02 |
| UN | 0.94 | 0.01 | nd | nd | nd |
| UN | 0.96 | 0.01 | 0.01 | nd | 0.01 |
| UN | 0.99 | 0.02 | 0.01 | 0.01 | 0.01 |
| UN | 2.01 | nd | nd | nd | 0.01 |
| ΣIMP (% IN) | | 0.22 | 0.17 | 0.13 | 0.16 |

| Pemetrexed. Arg 2 salt stability (Composition of Example 3) | | | | |
|---|---|---|---|---|
| Name | RRT | ZERO | 2 weeks 50° C. | 1 month 40° C./ 75% RH |
| Pemetrexed (% in) | 1.00 | 99.71 | 99.69 | 99.69 |
| L-arginine | 0.07 | 0.05 | 0.05 | 0.05 |
| imp_A | 0.78 | 0.04 | 0.04 | 0.04 |
| imp_D | 0.91 | <0.04% | <0.04% | <0.04% |
| UN | 0.92 | 0.10 | 0.08 | 0.08 |
| imp_B | 0.96 | <0.04% | <0.04% | <0.04% |
| imp_C | 0.98 | <0.04% | <0.04% | <0.04% |
| ΣIMP (≥0.04% IN) | | 0.19 | 0.17 | 0.17 |
| ΣIMP (<0.04% 1N) | | 0.10 | 0.14 | 0.14 |
| ΣIMP (% IN) | | 0.29 | 0.31 | 0.31 |

Result: pemetrexed-arginine salt in lyophilized composition is fully comparable to commercial pemetrexed disodium composition from stability point of view.

The invention claimed is:

1. Arginine salt of pemetrexed of formula (1)

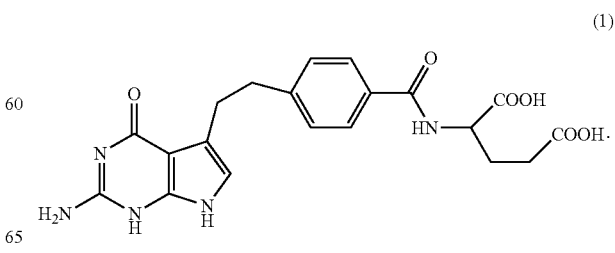

(1)

2. The salt according to claim 1 having the formula (2)

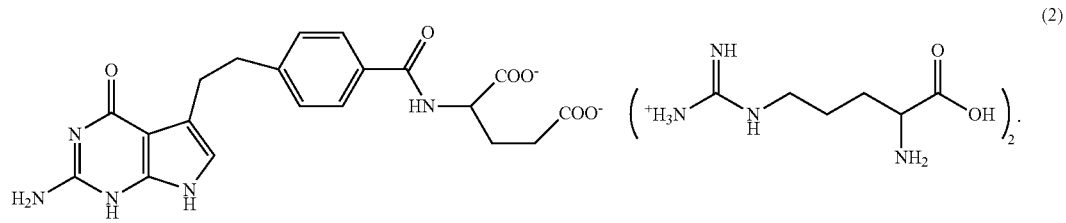

3. The salt according to claim 1 in solid form.
4. The salt according to claim 3, in amorphous form.
5. A pharmaceutical composition comprising the arginine salt of pemetrexed according to claim 1 and at least one pharmaceutically acceptable excipient.
6. The composition according to claim 5, which is a solid composition.
7. The composition according to claim 6 comprising the arginine salt of pemetrexed in an amorphous form.
8. The composition according to claim 5, which is a lyophilized powder useful for reconstitution into an infusion solution by an infusion liquid.
9. The composition according to claim 5, wherein the excipient is selected from the group consisting of: diluents or bulking agents; antibacterial preservatives; antioxidants; pH-adjustors; buffers; chelating agents; and tonicity contributors.
10. The composition according to claim 8, wherein the excipient is mannitol.
11. A process for making arginine salt of pemetrexed comprising combining pemetrexed diacid of formula (1)

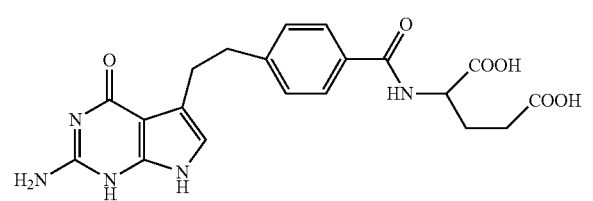

with L-arginine in a solution and removing the solvent.

12. The process according to claim 11, wherein the removal of the solvent is carried out by evaporation or lyophilization.
13. A process for making a pharmaceutical composition, comprising a step of combining arginine salt of pemetrexed with at least one pharmaceutically acceptable excipient.
14. The process according to claim 13, wherein the pharmaceutical composition is a solid composition.
15. The process according to claim 13, wherein the step of combining comprises providing arginine salt of pemetrexed, contacting it with excipient(s) in a solvent and removing the solvent.
16. The process according to claim 15, wherein the step of providing the arginine salt of pemetrexed comprises mixing pemetrexed diacid with arginine in a solvent.
17. The composition according to claim 9, wherein said excipient is selected from the group consisting of dextrose, sucrose, mannose, lactose, trehalose, mannitol, xylitol, thiomersal, benzalkonium chloride, benzethonium chloride, chlorobutanol, ascorbic acid, glutathione, L-cysteine, lipoic acid, hydrochloric acid, acetate buffer, citrate buffer, tartrate buffer, phosphate buffer, benzoate buffer, bicarbonate buffer, disodium edetate, sodium chloride, and potassium chloride.

* * * * *